US00PP23713P2

(12) United States Plant Patent
Osiecki

(10) Patent No.: US PP23,713 P2
(45) Date of Patent: Jul. 2, 2013

(54) ***SPATHIPHYLLUM* PLANT NAMED 'S43'**

(50) Latin Name: ***Spathiphyllum* hybrid**
Varietal Denomination: S43

(75) Inventor: Marian Osiecki, Marianna, FL (US)

(73) Assignee: Oglesby Plants International, Altha, FL (US)

( * ) Notice: Subject to any disclaimer, the term of this patent is extended or adjusted under 35 U.S.C. 154(b) by 0 days.

(21) Appl. No.: 13/200,510

(22) Filed: Sep. 23, 2011

(51) Int. Cl.
*A01H 5/00* (2006.01)

(52) U.S. Cl.
USPC ..... Plt./364

(58) Field of Classification Search
USPC ..... Plt./364
See application file for complete search history.

*Primary Examiner* — Susan McCormick Ewoldt
(74) *Attorney, Agent, or Firm* — Cassandra Bright

(57) ABSTRACT

A new and distinct *Spathiphyllum* cultivar named 'S43' is disclosed, characterized by dark green, glossy foliage, early foliage production and rapid, compact growth. The new variety maintains its dark green foliage color under higher than normal light conditions, or low nutrient levels. The new variety is commercially suitable for four and six inch pot production and responds to Gibberellic acid treatment by flowering in 9 weeks after treatment. The new variety is a *Spathiphyllum*, typically produced as an indoor ornamental plant.

1 Drawing Sheet

Latin name of the genus and species: *Spathiphyllum* hybrid.

Variety denomination: 'S43'.

BACKGROUND OF THE INVENTION

The new cultivar is a product of a planned breeding program. The objective of the breeding program was to develop new *Spathiphyllum* varieties suitable for 4 inch or 6 inch commercial pot production, and with fast growth, and dark green foliage. The new variety originated from a cross pollination of a proprietary, unpatented seed parent referred to as '03-3-1' and the pollen parent, 'Power Petite' U.S. Plant Pat. No. 15,649. The crossing was made during April 2005.

The new variety was discovered by the inventor, Marian Osiecki, a citizen of the US, in September 2006 in a group of seedlings resulting from the crossing. The new cultivar was found in a commercial greenhouse in Altha, Fla.

Asexual reproduction of the new cultivar 'S43' was first performed at a commercial laboratory in Altha, Fla. by tissue culture in April of 2007. Subsequent propagation by tissue culture has shown that the unique features of this cultivar are stable and reproduced true to type.

SUMMARY OF THE INVENTION

The cultivar 'S43' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'S43'. These characteristics in combination distinguish 'S43' as a new and distinct *Spathiphyllum* cultivar:

1. Very dark green, broad foliage.
2. Early production of secondary foliage, resulting in a full plant growth earlier.
3. Rapidly growing and short, compact growth habit.

4. Maintains very dark green color under higher than normal light conditions, or low nutrient levels.
5. Spathe production in response to Gibberellic Acid treatment after 9 weeks.
6. Plant habit suitable for 4 inch or 6 inch commercial pots.
7. High number of spathes produced on average.

PARENT COMPARISON

Plants of the new cultivar 'S43' are similar to the seed parent in most horticultural characteristics. The new variety, however, produces shorter, more compact plants. Additionally, 'S43' produces thicker, glossier, shorter, narrower leaf blades and shorter petioles than the seed parent. Spathes of 'S43' are smaller and closer to the foliage than the spathes of the seed parent. 'S43' has also shown better resistance to the diseases *Myrothecium* and leaf *Phytophthora* than the seed parent. 'S43' produces spathes earlier and more abundantly than '03-3-1'.

Plants of the new cultivar 'S43' are similar to the pollen parent 'Power Petite' U.S. Plant Pat. No. 15,649 in most horticultural characteristics. Plants of the new variety however are more vigorous and faster growing than 'Power Petite'. Additionally, 'S43' produces more leaves, and produces additional foliage earlier than 'Power Petite'. Plants of 'S43' are taller than plants of 'Power Petite'. Foliage of the two varieties differs; 'S43' produces wider, darker, more upright foliage with less undulation on the leaf blade than 'Power Petite'. Additionally, plants of 'S43' produce spathes earlier and more abundantly than 'Power Petite'. Plants of 'S43' respond after 9 weeks to the normal GA treatment given to commercial *Spathiphyllum* plants, whereas 'Power Petite' responds after 14 weeks. Spathes of 'S43' are produced closer to the foliage than those of 'Power Petite'.

COMMERCIAL COMPARISON

'S43' can be compared to compared to the commercial variety *Spathiphyllum* 'S9' U.S. Plant Pat. No. 9,901 Plants of 'S9' are similar to plants of 'S43' in most horticultural characteristics, however, plants of 'S43' are larger and faster growing than 'S9'. 'S43' has much darker, glossier leaves than 'S9'. Additionally 'S43' produces more shoots and has a wider leaf with a less undulating leaf margin than 'S9'. Spathes on plants of 'S43' are closer to the foliage than the spathes produced on plants of 'S9'.

'S43' can be compared to compared to the commercial variety *Spathiphyllum* '54905' U.S. Plant Pat. No. 13,718. Plants of '54905' are similar to plants of 'S43' in most horticultural characteristics, however, plants of 'S43' are shorter than plants of '54905'. 'S43' has much darker, glossier leaves that are shorter in length than foliage of '54905'. Additionally 'S43' produces foliage with an upright orientation, whereas foliage of '54905' is outwardly arched, creating a more open plant form. Spathes on plants of 'S43' are closer to the foliage than the spathes produced on plants of '54905' Spathes of 'S43' are more elongated compared to the rounder spathe shape of '54905'.

TABLE

| Variety | Serial Number Co-pending | Plant Height | Spathe width |
|---|---|---|---|
| 'S39' | 13/200,513 | 30 cm to top of foliar plane. 58 cm to top of spathe. | 6 cm |
| 'S40' | 13/200,514 | 35 cm to top of foliar plane. 65 cm to top of spathe. | 4.5 to 5.0 cm |
| 'S41' | 13/200,515 | 55 cm to top of foliar plant. 80 cm to top of spathe. | 6 to 8 cm |
| 'S42' | 13/200,509 | 45 cm to top of foliar plant. 65 cm to top of spathe. | 4 to 6 cm |
| 'S43' | 13/200,510 | 60 cm to top of foliar plant. 80 cm to top of spathe. | 5 to 7 cm |

| Variety | Spathe Length | Mature Spathe Color | Quantity of Leaves |
|---|---|---|---|
| 'S39' | 10-12 cm | Front: White 155C Back: White 155C | 70 to 90 in an average of 6 clumps |
| 'S40' | 9 to 12 cm | Front: Green-White 157C Back: Green-White 157C, veins and flush near veins Green 143C | 50 to 60 in an average of 4 to 5 clumps |
| 'S41' | 14 to 16 cm | Front: White 155C Back: White 155C mid vein near Green 143A | 40 to 65 in an average of 8 clumps. |
| 'S42' | 10 to 14 cm | Front: White 155C, but more clear white. Back: White 155C, but more clear white mid vein near Green 143A | 100 to 180 in an average of 12 to 15 clumps. |
| '843' | 12 to 14 cm | Front: White 155C, but more clear white. Back: White 155C, but more clear white mid vein near Green 143A | 60 to 100 in an average of 8 to 10 clumps. |

BRIEF DESCRIPTION OF THE PHOTOGRAPH

The accompanying photograph in FIG. 1 illustrates in full color a typical plant of 'S43' grown in a greenhouse in Altha, Fla. This plant is approximately 9 months old, shown in a 6 inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'S43' plants grown in a climate controlled greenhouse in Altha, Fla., USA. Temperatures ranged from 20° C. to 25° C. at night to 25° C. to 32° C. during the day. No artificial light, photoperiodic treatments were given to the plants. Plants were treated with Giberellic Acid at 200 ppm, to induce spathe production in approximately 9 weeks. Plants were grown in 80% shade, resulting in approximately 800 to 1200 foot candles of light. Measurements and numerical values represent averages of typical plant types.

Botanical classification: *Spathiphyllum* hybrid 'S43'.

PROPAGATION

Time to initiate roots: Approximately 14 days at approximately 25° C. soil temperature.

Time to produce a fully rooted plantlet: Approximately 12 weeks at approximately 25 to 30° C. soil temperature.

Root description: Thick, fleshy roots with fine, fibrous lateral roots. Color near Orange-White 158D.

PLANT

Growth habit: Leaves growing directly from base of plant, with no stems.

Plant shape: Upright, leaves arching out to nearly horizontal.

Height: Approximately 60 cm to top of foliar plane. Approximately 80 cm to top of tallest spathe.

Plant spread: Approximately 95 cm in a 6 inch pot.

Normal pot size: 6 inch and larger.

Growth rate: Moderate.

Branching characteristics: No branching. Leaves emerge direct from base of plant.

Number of clumps of leaves: 8 to 10.

Number of leaves per clump: Average 8 to 10.

Number of leaves per plant: Approximately 60 to 100.

Age of plant described: Approximately 9 months.

FOLIAGE

Leaf:

*Arrangement*.—Single leaves emerging basally.

*Average length* (*excluding petiole of fully expanded leaf*).—Approximately 30 cm.

*Average width*.—Approximately 14 cm.

*Shape of blade*.—Ovate.

*Aspect*.—Slightly undulating, mainly at margin, entire leaf slightly recurved.

*Apex*.—Moderately cirrose.

*Base*.—Rounded.

*Margin*.—Entire.

*Texture of top surface*.—Smooth, glossy.

*Texture of bottom surface*.—Smooth, glossy.

*Color*.—Young foliage upper side: Near R.H.S. Green139A, but darker. Young foliage under side: Near R.H.S. Green 137A. Mature foliage upper side: Near R.H.S. Green139A. Mature foliage under side: Near R.H.S. Green 137A.

Venation:

*Type*.—Pinnate.

*Venation coloration upper side*.—Near RHS Green 139A.

*Venation coloration under side*.—Near RHS Yellow-Green 144B.

Petiole:
*Length*.—Approximate range between 20 and 30 cm.
*Width*.—At geniculum: Approximately 0.7 cm. Above clump: Approximately 1.6 cm.
*Color*.—Near RHS Green 139A.
*Strength*.—Strong.
*Other*.—Petiole wing present.
Geniculum:
*Length*.—Approximately 2.8 cm.
*Width*.—Approximately 0.7 cm.
*Color*.—Near RHS Green 138A.
Petiole wing/petiole sheath:
*Length*.—Approximately same length as individual petiole.
*Width*.—Approximately 0.4 to 1.0 cm.
*Color*.—Near RHS Green 139A.

INFLORESCENCE.

Arrangement: Spathes with spadices held above the foliage on erect peduncles arising from the petiole sheath.
Flowering habit: Continuous.
Quantity of spathes per plant: On average 6 spathes in good condition.
Natural flowering season: Plants are normally treated with Gibberellic Acid to induce flowers year round.
Fragrance: None.
Self-cleaning or persistent: Persistent.
Flower longevity: Flowers stay in good condition approximately 5 weeks on the plant.
Spathe:
*Aspect*.—Cupped.
*Length*.—Approximately 12 to 14 cm.
*Width*.—Approximately 5.0 to 7.0 cm.
*Shape*.—Ovate.
*Margin*.—Entire.
*Apex*.—Apiculate.
*Base*.—Cuneate, non-symmetrical.
*Color*.—Front when opening: Near RHS White 155C, but more clear white. Back when opening: Near RHS White 155C, but more clear white. Mid vein near Green 143A. Front when mature: Near RHS White 155C, but more clear white. Back when mature: Near RHS White 155C, but more clear white mid vein near Green 143A. Front Fading to: Near RHS Yellow-Green 144D. Back Fading to: Near RHS Green 145B, mid vein Green 143A.
Spadix:
*Shape*.—Columnar, arising from the top of the peduncle.
*Tip*.—Obtuse.
*Base*.—Obtuse.
*Length*.—Approximately 8.0 cm.
*Width*.—Approximately 1.8 cm.
*Color*.—When opening: Near RHS White 155D. Mature: Near RHS Green 144A.
*Quantity of flowers per spadix*.—Approximately 215.
*Spadix flower arrangement*.—Bisexual, rounded.
*Spadix flower description*.—Flowers completely compressed and diminished to the point of not measurable.
Peduncle:
*Length*.—Approximately 30 cm, measured from base, which emerges from leaf axil.
*Width*.—Approximately 0.5 cm.
*Color*.—Near RHS Green 137A.
*Strength*.—Very strong.

REPRODUCTIVE ORGANS

All flower parts and reproductive organs are highly reduced, to the point of not measurable:
*Quantity of pollen*.—Moderate.
*Pollen color*.—Near RHS 155D.

OTHER CHARACTERISTICS

Disease resistance: Neither resistance nor susceptibility to diseases or pests has been observed in this variety.
Drought tolerance and cold tolerance: The new cultivar is a typical *Spathiphyllum*, cold tolerant to approximately 5 to 7° C. and does not tolerate drought.
Fruit/seed production: Not observed.

What is claimed is:

1. A new and distinct cultivar of *Spathiphyllum* plant named 'S43' as herein illustrated and described.

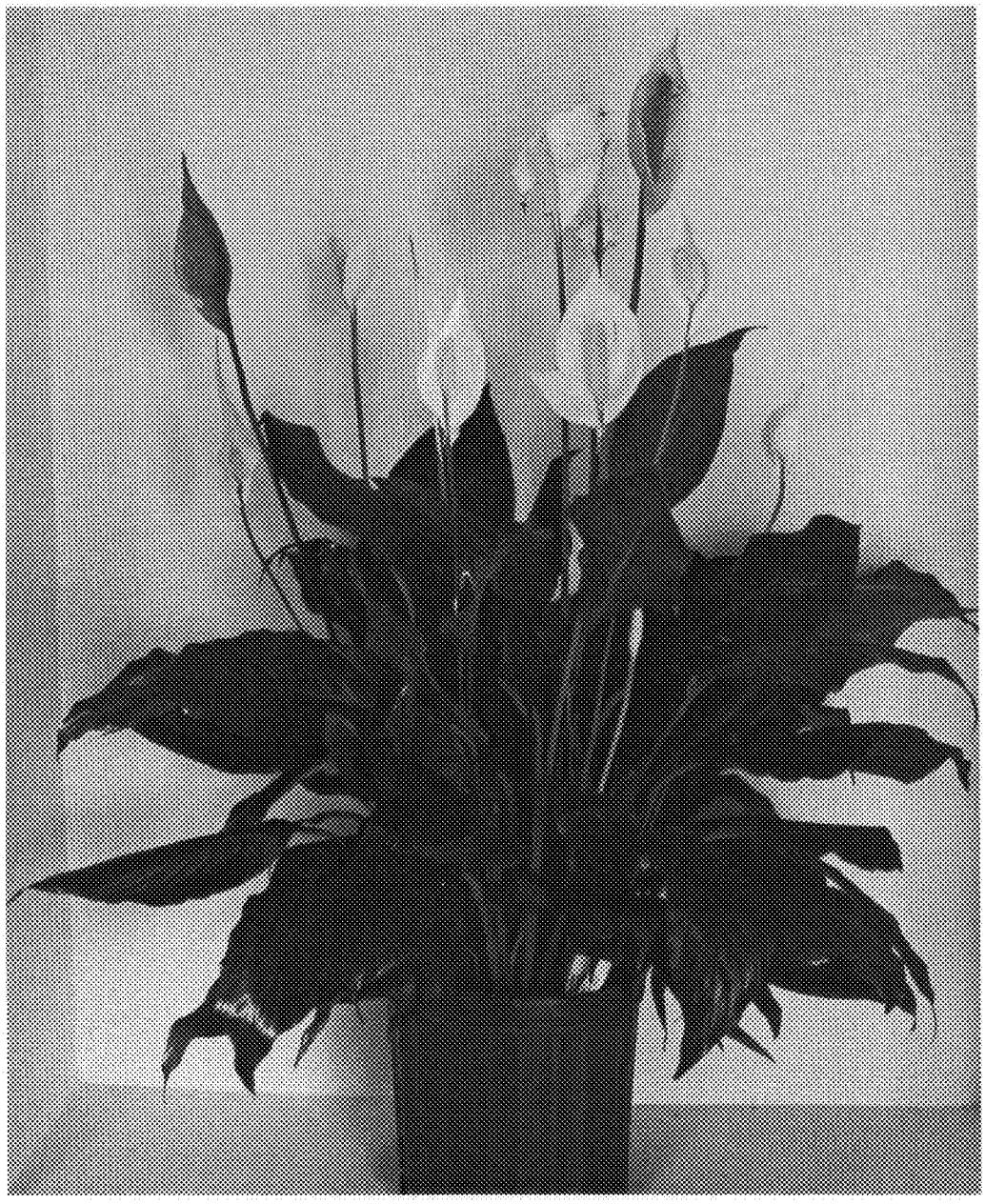

* * * * *